United States Patent [19]

Wielhouwer et al.

[11] 4,344,758

[45] Aug. 17, 1982

[54] DENTAL FACE SHIELD

[75] Inventors: Sandra L. Wielhouwer, Union Lake; Suzanne M. Fortner, Farmington Hills, both of Mich.

[73] Assignee: John D. Wielhouwer, Union Lake, Mich.

[21] Appl. No.: 251,175

[22] Filed: Apr. 6, 1981

[51] Int. Cl.³ .............................................. A61C 5/14
[52] U.S. Cl. ..................................... 433/137; 433/136
[58] Field of Search ............... 128/206.14, 28, 202.28; 433/137, 136

[56] References Cited

U.S. PATENT DOCUMENTS

| | | | |
|---|---|---|---|
| 531,094 | 12/1894 | Bronson | 248/141 |
| 835,432 | 11/1906 | Hughes | 433/137 |
| 1,850,540 | 3/1932 | Erickson | 132/88.5 |
| 2,667,869 | 2/1954 | D'Elia | 128/147 |
| 2,695,622 | 11/1954 | Herod et al. | 132/88.5 |
| 2,928,388 | 3/1960 | Jaroslaw | 128/206.14 |
| 3,364,928 | 1/1968 | Creager, Jr. et al. | 128/132 |
| 3,478,432 | 11/1969 | Gross | 433/137 |
| 3,561,440 | 2/1971 | Bayer | 128/132 |
| 3,667,458 | 6/1972 | Krebs | 128/132 |
| 3,669,106 | 6/1972 | Schrading et al. | 128/132 D |
| 3,826,253 | 7/1974 | Larsh et al. | 128/132 D |
| 3,916,887 | 11/1975 | Kelly | 128/132 D |
| 3,956,048 | 5/1976 | Nordgren | 156/183 |
| 4,024,862 | 5/1977 | Collins | 128/132 D |
| 4,050,457 | 9/1977 | Davidson | 128/145.5 |

*Primary Examiner*—Robert Peshock
*Attorney, Agent, or Firm*—Harness, Dickey & Pierce

[57] ABSTRACT

A face shield for use during operations in the fields of dentistry and dental hygiene having an absorbent exterior surface layer, a barrier surface layer, an aperture through both layers, and a moisture-resistant adhesive attachment mechanism to form a seal against moisture when the shield is applied to the face of a patient and a moisture spray is directed toward the patient as that utilized with various tools used in these fields. The face shield is also pliable and has an aperture to permit a degree of freedom of movement for the patient's mouth when the face shield is disposed in its operative position.

13 Claims, 5 Drawing Figures

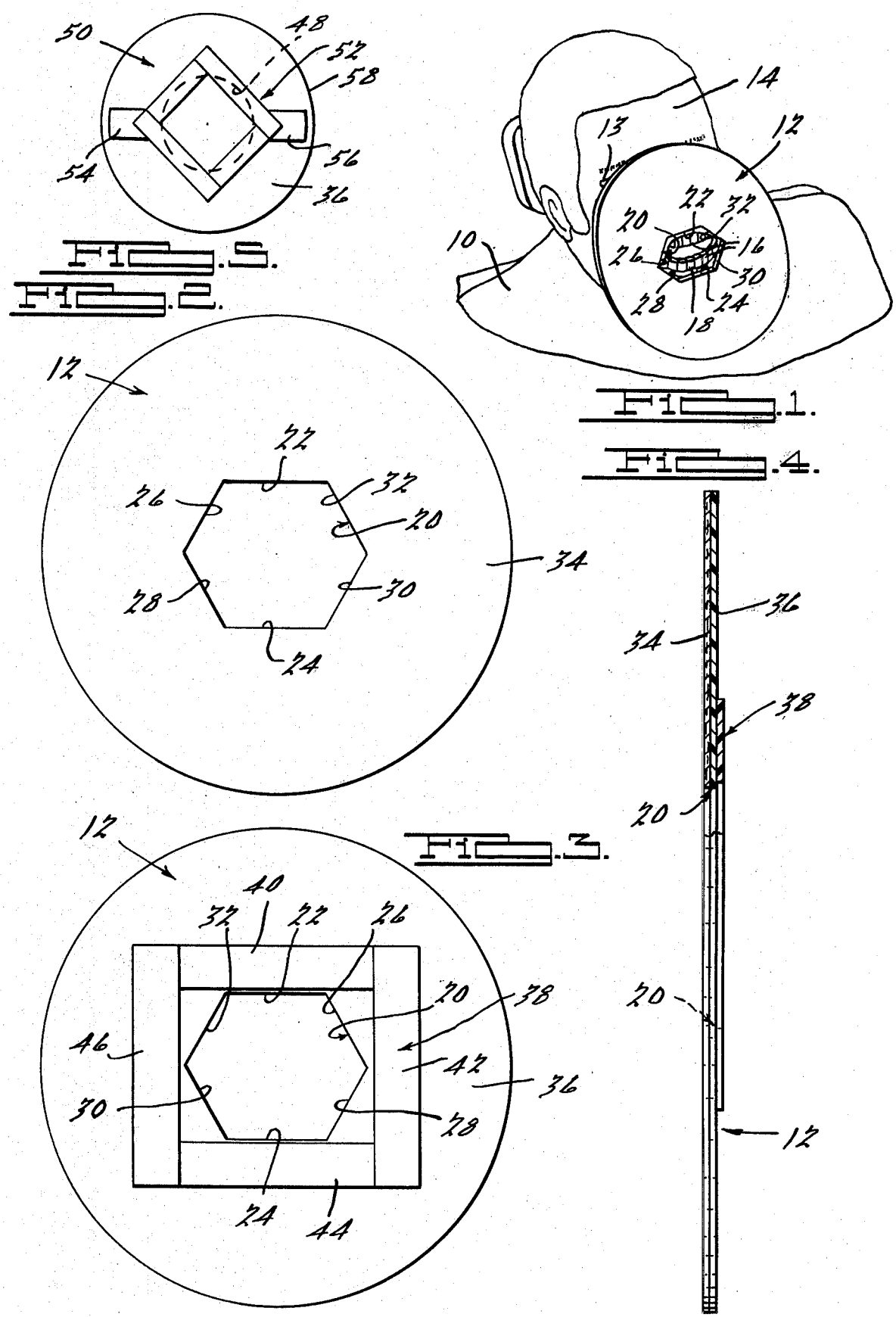

DENTAL FACE SHIELD

BACKGROUND AND SUMMARY OF THE INVENTION

The present invention relates generally to a face shield for use during operations in the fields of dentistry and dental hygiene and particularly for use with dental or dental hygiene operations in which a spray of fluid is directed toward a patient's mouth during the course of the operation.

With the advent of vibratory machines and the like for scaling calculus from teeth and the implementation of the cooling mechanism of a spray of water directed into the mouth by the machine during the course of the operation, a particular degree of discomfort to the patient has been realized from the spray of water leaving the patient's face wet, the patient not being able to open his eyes at any time during the course of the operation due to the spray of water directed at them, and the general feeling that the patient has after not only withstanding the discomfort of the operation, but also including the aftermath of an irritable feeling due to the dampness of his hair and any other part of his body that has not been draped in addition to the discomfort he has with his teeth. Draping of the hair and face is not economical and also would make the operation more burdensome for the dental hygienist or dentist.

The present invention is directed to provide the advantage of comfort during such an operation where fluid for cooling, cleaning debris, etc., is used and directed toward the patient's mouth. The present invention has a barrier surface adjacent the patient's skin surface and an absorbent surface exterior to that barrier surface to absorb moisture and keep it from running down the barrier surface. The attachment means of the present invention also provides the advantage of sealing the patient from receiving any moisture which would cause him discomfort along his face, facial hair, and/or scalp areas. The face shield furthermore permits the patient to open his eyes and look about during the course of the operation while shielding his eyes from any direct flow of water toward them, and is pliable to permit facial movements when in its operative position.

All the above features are also provided in an inexpensive yet sterile, storable device.

Other objects and advantages of the instant invention will be apparent from the following specification, claims and drawings.

BRIEF DESCRIPTION OF THE DRAWINGS

FIG. 1 is an elevated perspective view of the dental face shield of the present invention mounted on a patient sitting in a dentist chair;

FIG. 2 is an elevated front view of the dental face shield of FIG. 1;

FIG. 3 is an elevated rear view of the device of FIG. 2;

FIG. 4 is a side sectional view of the device of FIG. 2; and

FIG. 5 is an elevated rear view of an alternative embodiment of the face shield of FIG. 2.

DESCRIPTION OF THE PREFERRED EMBODIMENT

Referring to FIG. 1, a patient 10 is illustrated having a face shield 12 situated thereon in an operative position upon the patient's face 14 wherein the patient's teeth 16 and gums 18 are exposed to a dentist or dental hygienist through an aperture 20 in the face shield 12. The patient 10 has his eyes 13 shielded by the face shield 12, but the shield 12 is spaced from the patient's eyes 13 to allow the eyes to be opened and also allow the patient to look around during the dental operation. The face shield 12 illustrated is circular in shape, but the invention is not to be limited to any particular shape. The aperture 20 as illustrated is large enough to permit the patient 10 to open his mouth within the aperture 20. In the preferred embodiment illustrated in FIG. 1 for an adult patient, the shield 12 has a diameter of approximately eight inches and the aperture is in the form of an elongated hexagon having the upper and lower sides 22, 24 thereof of approximately 2 inches in length and all other sides 26, 28, 30, 32 thereon of approximately one and one-half inches in length. Circular apertures and other configurations have also been found to function in an acceptable manner. A smaller size face shield would be used for patients who are children, with an appropriately scaled down aperture with the hexagon having sides of a length approximately one-fourth to one-sixth the diameter (or largest dimension) of the face shield.

Referring to FIGS. 2, 3 and 4, the face shield 12 is shown separated from the patient. Referring to FIG. 3, the pliable laminated composition of the face shield 12 is illustrated wherein an exterior absorbing means or absorbent surface 34 is laminated to an interior barrier surface 36. Adhesive attachment means 38 is then laminated to the barrier surface 36. The composition of the exterior absorbent surface 34 may be any relatively thin absorbent material having high moisture-absorbing qualities, such as paper toweling, as in particular that material sold under the trademark "Bolt". Barrier surface 36 is preferably a plastic-coated towel material or the like, such as that currently sold under the trade name "Veratex". The adhesive attachment means 28 illustrated in the preferred embodiment is a moisture-resistant tape such as that sold by Minnesota Mining & Manufacturing Co. as Secured Transparent Roll Tape under the trade name "New Man", comprising four pieces of tape 40, 42, 44, 46 in the form of a quadrilateral surrounding the aperture 20. It is intended, however, that either a one-piece or multiple piece adhesive attachment means be within the scope of the present invention.

The adhesive attachment means 38 is preferably laminated to the barrier surface 36 in an arrangement such that it surrounds the aperture 20 along the interior surface of the face shield 12, as shown in FIG. 3. The materials may be laminated by any of several methods known to those skilled in the art (adhesive, double-sided tape, etc.). The adhesive attachment means 38 is preferably continuous such that when the face shield 12 is applied to the patient's face 14, a watertight seal is formed around the mouth of the patient 10. If a multiple piece adhesive attachment means is employed, some overlap of the pieces would be preferred to make certain that the continuity exists. A disposable protective cover paper is placed over the attachment means or tape 38 prior to use on a patient.

An alternative embodiment is illustrated in FIG. 5. In this embodiment, a larger aperture 48 is used in the face shield 50, wherein more freedom of movement may be available to the patient 10. The adhesive attachment means 52, however, has a portion extending within the aperture 48 to make the aperture 48 smaller at those points without restricting the freedom of movement of the patient. Additional disposable protective cover paper may be used to cover the portion of the attachment means accessible from the absorbing means 34 (exterior) side of the face shield 12. In addition, the adhesive attachment means 52 further comprises two portions 54, 56 extending from said aperture 48 toward the outer edge 58 of the face shield 50. These portions will further secure the face shield 50 to the patient's face 14 while also presenting a face shield 50 more contoured to the patient's face 14 and less likely for inadvertent contact with the hand or instruments of the dental hygienist or dentist operating on the patient.

It can be seen from the foregoing that the present invention provides a new and improved face shield which embodies a number of features not shown in the prior art. In particular, the pliable face shield of the present invention allows the patient freedom of movement while also providing a moisture-resistant seal around the patient's mouth and absorbing moisture directed toward the patient's face and hair on its exterior while protecting said moisture from reaching the patient's face and hair, and preventing discomfort thereto adjacent the interior surfaces of the face shield.

While it will be apparent that the preferred embodiment of the invention disclosed is well calculated to fulfill the objects above stated, it will be appreciated that the invention is susceptible to modification, variation and change without departing from the proper scope or fair meaning of the subjoined claims.

What is claimed is:

1. A face shield for use on a patient's face in dental operations, comprising
   means for absorbing moisture providing the exterior surface of said shield directed away from the face;
   barrier means disposed adjacent said absorbing means providing an interior protective surface directed towards the face;
   adhesive attachment means secured to said barrier means, said adhesive attachment means being substantially unaffected as to its adhesive capacity by moisture;
   an aperture disposed through said absorbing means and said barrier means of a size large enough for the patient's open mouth; and
   said barrier means and said absorbing means extending outwardly from said aperture and said adhesive attachment means in a direction away from the patient's mouth.

2. A claim in accordance with claim 1, wherein said adhesive attachment means forms a seal around the mouth of a patient when operably disposed on the patient's face.

3. A claim in accordance with claim 1, wherein said aperture is in the shape of a hexagon to accommodate movement of the patient's mouth and approximate the shape of a patient's open mouth.

4. A claim in accordance with claim 3, wherein said aperture is in the form of an elongated hexagon.

5. A claim in accordance with claim 4, wherein for an adult patient, said shield is circular in shape with a diameter of approximately eight inches and said hexagon aperture has two elongated sides of approximately two inches and four sides of approximately one and one-half inches.

6. A claim in accordance with claim 3, wherein each side of the hexagon have a length in the range of approximately one-fourth to approximately one-sixth the largest dimension of said shield.

7. A claim in accordance with claim 1, wherein said adhesive attachment means comprises a moisture-resistant adhesive tape.

8. A claim in accordance with claim 7, wherein said adhesive attachment means comprises a square formed by said tape around said aperture.

9. A claim in accordance with claim 8, wherein a portion of said square of tape extends within said aperture.

10. A claim in accordance with claim 7, wherein said adhesive attachment means includes at least one tape portion extending from adjacent said aperture toward the periphery of said face shield.

11. A claim in accordance with claim 1, wherein both said absorbing means and said barrier means are pliable.

12. A face shield for use on a patient's face in dental operations, comprising
    means for absorbing moisture providing an exterior surface of said shield directed away from the face;
    barrier means disposed adjacent said absorbing means providing an interior surface directed towards the face;
    an aperture disposed through said absorbing means and said barrier means of a size large enough for the patient's open mouth, said absorbing means and said barrier means extending radially outwardly from said aperture; and
    adhesive sealing and attachment means disposed at least substantially at the edge of said aperture, said adhesive sealing and attachment means being substantially unaffected as to its adhesive capacity by moisture and sealing the periphery of the patient's mouth to keep moisture limited to the mouth area of the patient's face during a dental operation.

13. A face shield for use on a patient's face in dental operations, comprising
    means for absorbing moisture providing at least a portion of the exterior surface of said shield, directed away from the face;
    barrier means disposed adjacent said absorbing means providing an interior protective surface directed towards the face;
    an aperture disposed through said barrier means and through at least a portion of said absorbing means of a size large enough for the patient's open mouth; and
    adhesive sealing and attachment means, said adhesive means being substantially unaffected as to its adhesive capacity by moisture and sealing around the outer periphery of the patient's mouth to prevent moisture from the mouth area from becoming disposed between the barrier means and the patient's face during a dental operation.

* * * * *